(12) United States Patent
Liu et al.

(10) Patent No.: US 11,577,219 B2
(45) Date of Patent: Feb. 14, 2023

(54) METHOD FOR PREPARING NATURAL ORGANIC MACROMOLECULAR WATER TREATMENT AGENT

(71) Applicant: Hebei University of Environmental Engineering, Qinhuangdao (CN)

(72) Inventors: Jun Liu, Qinhuangdao (CN); Yuguo Zhuo, Qinhuangdao (CN); Jinming Zhuo, Qinhuangdao (CN)

(73) Assignee: Hebei University of Environmental Engineering

( * ) Notice: Subject to any disclaimer, the term of this patent is extended or adjusted under 35 U.S.C. 154(b) by 73 days.

(21) Appl. No.: 17/383,618

(22) Filed: Jul. 23, 2021

(65) Prior Publication Data

US 2022/0062856 A1    Mar. 3, 2022

(30) Foreign Application Priority Data

Sep. 2, 2020   (CN) .......................... 202010910572.9

(51) Int. Cl.

| | |
|---|---|
| *B01J 20/24* | (2006.01) |
| *B01J 20/10* | (2006.01) |
| *B01J 20/28* | (2006.01) |
| *B01J 20/291* | (2006.01) |
| *B01J 20/30* | (2006.01) |
| *C02F 1/28* | (2023.01) |
| *C08L 3/02* | (2006.01) |
| *C08L 3/12* | (2006.01) |
| *B82Y 5/00* | (2011.01) |
| *B82Y 40/00* | (2011.01) |

(52) U.S. Cl.
CPC ............. *B01J 20/24* (2013.01); *B01J 20/103* (2013.01); *B01J 20/28007* (2013.01); *B01J 20/291* (2013.01); *B01J 20/3007* (2013.01); *B01J 20/3078* (2013.01); *C02F 1/288* (2013.01); *C08L 3/02* (2013.01); *C08L 3/12* (2013.01); *B01J 2220/4825* (2013.01); *B01J 2220/68* (2013.01); *B82Y 5/00* (2013.01); *B82Y 40/00* (2013.01)

(58) Field of Classification Search
CPC ...... B01J 20/24; B01J 20/291; B01J 20/3007; B01J 20/3078; B01J 2220/4825; B01J 2220/68; C02F 1/288; C08L 3/02; C08L 3/12; B82Y 5/00; B82Y 40/00
USPC ........................................................ 502/404
See application file for complete search history.

(56) References Cited

U.S. PATENT DOCUMENTS

2015/0352520 A1\* 12/2015 Suarez-Hernandez ......................
B01J 20/3014
502/402

\* cited by examiner

*Primary Examiner* — Edward M Johnson
(74) *Attorney, Agent, or Firm* — Lerner, David, Littenberg, Krumholz & Mentlik, LLP

(57) ABSTRACT

Method for preparing a natural organic macromolecular water treatment agent including: dissolving amylose corn starch in an alkali solution, stirring for 30 min, to obtain a suspension, freezing the suspension to fully frozen state, melting and dialyzing, to obtain a corn starch dispersion; mixing a modified flax fiber, the dispersion, nano-hybrid silica and distilled water, performing 800 W ultrasonication for 10 min, to obtain a treated suspension; taking an amount of a superabsorbent macromolecular resin with a certain shape, making it absorb water and swell into a solid hydrogel with the certain shape; mixing the solid hydrogel and the treated suspension, static defoaming, loading into a mold and solidifing, drying until the solid hydrogel is completely dehydrated, to obtain a hollow agent; spraying a catalytic degrading agent/toxin degrading agent on the surface of the hollow agent and/or the inner wall of holes thereof, to obtain the target agent.

6 Claims, No Drawings

METHOD FOR PREPARING NATURAL ORGANIC MACROMOLECULAR WATER TREATMENT AGENT

CROSS REFERENCE TO RELATED APPLICATION

This patent application claims the benefit and priority of Chinese Patent Application No. 202010910572.9 filed on Sep. 2, 2020, the disclosure of which is incorporated by reference herein in its entirety as part of the present application.

TECHNICAL FIELD

The present disclosure relates to the technical field of water treatment, and in particular to a method for preparing a natural organic macromolecular water treatment agent.

BACKGROUND ART

In recent years, with the gradual increase of the discharge of industrial and agricultural wastewater and municipal sewage, the rivers, lakes and reservoirs in China are generally polluted to varying degrees, and the water quality is deteriorating, causing serious harm to the ecological environment and human health.

Traditional methods for wastewater treatment include ion exchange method, solvent extraction method, chemical precipitation method, oxidation-reduction method, adsorption method, electrochemical treatment method and membrane technology method. Most of the methods, however, have the problems such as large dosage of chemicals, high cost, unsatisfactory effect, and being prone to secondary pollution. Among these methods, the adsorption method is simple for operation, and has low cost and high efficiency.

Currently, it has become a research hotspot to develop an adsorbent that is non-toxic, and has low cost, high efficiency and strong complexing capacity. The use of natural macromolecular compounds, agricultural and forestry wastes, and industrial by-products as the adsorbent in wastewater treatment has attracted more and more attention.

SUMMARY

An object of the present disclosure is to provide a method for preparing a natural organic macromolecular water treatment agent. The prepared water treatment agent exhibits strong adsorption capacity, and it could realize the rapid and effective degradation of harmful substances, having a wide range of application.

In order to achieve the above object, the present disclosure provides the following technical solutions:

A method for preparing a natural organic macromolecular water treatment agent, comprising:

S1, dissolving amylose corn starch in an alkali solution, stirring for 30 min, to obtain a suspension, and freezing the suspension to a fully frozen state, to obtain a frozen product, melting the frozen product, and subjecting the melted frozen product to a dialysis treatment, to obtain a corn starch dispersion;

S2, mixing 50 mg of a modified flax fiber, 50 mg of the corn starch dispersion, 20 mg of nano-hybrid silica and 5 mL of distilled water, to obtain a mixture, and subjecting the mixture to an ultrasonic treatment with 800 W for 10 min, to obtain an ultrasonic treated suspension;

S3, taking an appropriate amount of a superabsorbent macromolecular resin with a certain shape, making the superabsorbent macromolecular resin fully absorb water and swell, to form a solid hydrogel with the certain shape;

S4, uniformly mixing the solid hydrogel and the ultrasonic treated suspension in a mass ratio of 1:(2.5-10.5), subjecting the resulting mixture to a static defoaming, then loading into a mold and solidifing, and drying until the solid hydrogel is completely dehydrated, to obtain a hollow water treatment agent; and S5, spraying a catalytic degrading agent and/or toxin degrading agent on the surface of the hollow water treatment agent and/or the inner wall of holes thereof, to obtain the natural organic macromolecular water treatment agent.

In some embodiments, in the step S1, the freezing is performed at a temperature of $-5°$ C. to $-15°$ C., and the freezing is performed for 30-50 min, and the melting is performed at ambient temperature and pressure.

In some embodiments, the modified flax fiber is prepared by:

washing a waste flax residue, and placing in an oven at 70° C. and drying to a constant weight, crushing, and sieving with a 200 mesh sieve, to obtain a flax powder; and immersing 3-5 parts by mass of the flax powder into 20-30 parts by mass of a NaOH solution with a mass concentration of 1 mol/L, to obtain a mixture, placing the mixture on a heating magnetic stirrer for magnetic stirring for 10 hours, and filtering, to obtain a filter residue, rinsing the filter residue with deionized water until the pH of rinse water is close to neutral, drying in a oven at 80° C., naturally cooling to ambient temperature, and drying in a oven, to obtain the modified flax fiber.

In some embodiments, the nano-hybrid silica is a nano-$SiO_2$ hybrid particle grafted with a chain segment of polyhydroxyethyl acrylate (PHEA) and polystyrene (PS).

In some embodiments, in the step S3, the superabsorbent macromolecular resin is selected from the group consisting of polyacrylic acid salt, polyvinyl alcohol, polyoxylated alkanes and cellulose.

In some embodiments, the toxin degrading agent is toxin degrading enzyme and/or toxin degrading bacteria.

The present disclosure has the following beneficial effects:

In the present disclosure, the solid hydrogel formed by making a superabsorbent macromolecular resin with a certain shape fully absorb water and swell is used as a pore-forming agent, enabling the wastewater treatment agent to be covered with various sizes of holes, which could significantly increase the contact area between the wastewater and the water treatment agent, thereby greatly improving the water treatment effect.

Based on the combination of the nano-hybrid silica, the modified flax fiber, nano-sized starch and the catalytic degradation agent or toxin degradation agent, the wastewater treatment agent could be given strong adsorption performance, and meanwhile, also makes it possible to realize the rapid and effective degradation of harmful substances, having a wide range of application.

DETAILED DESCRIPTION OF THE EMBODIMENTS

In order to make the objects and advantages of the present disclosure clearer, the present disclosure will be further illustrated in detail with reference to the specific examples. It should be understood that the examples described herein are only to explain the present disclosure but should not be intended to limit the present disclosure.

In the following examples, the modified flax filter was prepared by the following procedures:

The waste flax residues were washed with tap water and distilled water, and placed in an oven at 70° C. and dried to a constant weight, crushed, and sieved with a 200 mesh sieve, obtaining a flax power.

3-5 parts by mass of the flax powder were immersed into 20-30 parts by mass of NaOH solution with a mass concentration of 1 mol/L, and placed on a heating magnetic stirrer for magnetic stirring for 10 hours. The resulting mixture was filtered, obtaining a filter residue. The filter residue was rinsed with deionized water until the pH of rinse water was close to neutral, and dried in a oven at 80° C., naturally cooled to ambient temperature, and dried in a drying oven, obtaining the modified flax fiber.

The nano-hybrid silica was nano-$SiO_2$ hybrid particles grafted with a chain segment of polyhydroxyethyl acrylate (PHEA) and polystyrene (PS).

The superabsorbent macromolecular resin was selected from the group consisting of polyacrylic acid salt, polyvinyl alcohol, polyoxylated alkanes and cellulose.

Example 1

The method for preparing a natural organic macromolecular water treatment agent was performed as follows:

S1, amylose corn starch was dissolved in an alkali solution, and stirred for 30 min, obtaining a suspension. The suspension was froze at −5° C. to −15° C. for 30-50 min to a fully frozen state, obtaining a frozen product. The frozen product was melted, obtaining a starch solution. The starch solution was subjected to a dialysis treatment (i.e. the starch solution was placed in a dialysis bag and dialyzed with ultrapure water for 7-9 days, in which the ultrapure water was changed every 6 to 12 hours; the relative molecular mass intercepted by the dialysis bag was 3500-14000, and the dialysis bag was made of cellulose acetate or regenerated cellulose), obtaining a corn starch dispersion.

S2, 50 mg of the modified flax fiber, 50 mg of the corn starch dispersion, 20 mg of the nano-hybrid silica and 5 mL of distilled water were mixed, obtaining a mixture, and the mixture was subjected to an ultrasonic treatment with 800 W for 10 min, obtaining an ultrasonic treated suspension.

S3, An appropriate amount of the superabsorbent macromolecular resin with a certain shape was taken, and it fully absorbed water and swelled, forming a solid hydrogel with the certain shape.

S4, The solid hydrogel and the ultrasonic treated suspension were uniformly mixed according to the mass ratio of 1:2.5. The resulting mixture was subjected to a static defoaming, then loaded into a mold and solidified, and dried until the solid hydrogel was completely dehydrated, obtaining a hollow water treatment agent.

S5, A catalytic degrading agent was sprayed onto the surface of the obtained hollow water treatment agent and/or the inner wall of the holes thereof, obtaining the natural organic macromolecular water treatment agent.

Example 2

The method for preparing a natural organic macromolecular water treatment agent was performed as follows:

S1, amylose corn starch was dissolved in an alkali solution, and stirred for 30 min, obtaining a suspension. The suspension was froze at −5° C. to −15° C. for 30-50 min to a fully frozen state, obtaining a frozen product. The frozen product was melted, obtaining a starch solution. The starch solution was subjected to a dialysis treatment (i.e. the starch solution was placed in a dialysis bag and dialyzed with ultrapure water for 7-9 days, in which the ultrapure water was changed every 6 to 12 hours; the relative molecular mass intercepted by the dialysis bag was 3500-14000, and the dialysis bag was made of cellulose acetate or regenerated cellulose), obtaining a corn starch dispersion.

S2, 50 mg of the modified flax fiber, 50 mg of the corn starch dispersion, 20 mg of the nano-hybrid silica and 5 mL of distilled water were mixed, obtaining a mixture, and the mixture was subjected to an ultrasonic treatment with 800 W for 10 min, obtaining an ultrasonic treated suspension.

S3, An appropriate amount of the superabsorbent macromolecular resin with a certain shape was taken, and it fully absorbed water and swelled, forming a solid hydrogel with the certain shape.

S4, The solid hydrogel and the ultrasonic treated suspension were uniformly mixed according to the mass ratio of 1:10.5. The resulting mixture was subjected to a static defoaming, then loaded into a mold and solidified, and dried until the solid hydrogel was completely dehydrated, obtaining a hollow water treatment agent.

S5, A toxin degrading agent was sprayed onto the surface of the obtained hollow water treatment agent and/or the inner wall of the holes thereof, obtaining the natural organic macromolecular water treatment agent. The toxin degrading agent was toxin degrading enzyme and/or toxin degrading bacteria.

Example 3

The method for preparing a natural organic macromolecular water treatment agent was performed as follows:

S1, amylose corn starch was dissolved in an alkali solution, and stirred for 30 min, obtaining a suspension. The suspension was froze at −5° C. to −15° C. for 30-50 min to a fully frozen state, obtaining a frozen product. The frozen product was melted, obtaining a starch solution. The starch solution was subjected to a dialysis treatment (i.e. the starch solution was placed in a dialysis bag and dialyzed with ultrapure water for 7-9 days, in which the ultrapure water was changed every 6 to 12 hours; the relative molecular mass intercepted by the dialysis bag was 3500-14000, and the dialysis bag was made of cellulose acetate or regenerated cellulose), obtaining a corn starch dispersion.

S2, 50 mg of the modified flax fiber, 50 mg of the corn starch dispersion, 20 mg of the nano-hybrid silica and 5 mL of distilled water were mixed, obtaining a mixture, and the mixture was subjected to an ultrasonic treatment with 800 W for 10 min, obtaining an ultrasonic treated suspension.

S3, An appropriate amount of the superabsorbent macromolecular resin with a certain shape was taken, and it fully absorbed water and swelled, forming a solid hydrogel with the certain shape.

S4, The solid hydrogel and the ultrasonic treated suspension were uniformly mixed according to the mass ratio of 1:6.5. The resulting mixture was subjected to a static defoaming, then loaded into a mold and solidified, and dried until the solid hydrogel was completely dehydrated, obtaining a hollow water treatment agent.

S5, A catalytic degrading agent and a toxin degrading agent was sprayed onto the surface of the obtained hollow water treatment agent and/or the inner wall of the holes thereof, obtaining the natural organic macromolecular water treatment agent. The toxin degrading agent was toxin degrading enzyme and/or toxin degrading bacteria. The toxin degrading agent was toxin degrading enzyme and/or toxin degrading bacteria.

When the above examples are used, the water treatment agent is added into a wastewater with a mass ratio of 20%, and subjected to a reaction while stirring for 3 h to 5 h, and filtered, thereby realizing the wastewater treatment.

The above description is only a preferred embodiment of the present disclosure. It should be pointed out that for those of ordinary skill in the art, several improvements and refinements could be made without departing from the principle of the present disclosure, and these improvements and refinements should fall within the protection scope of the present disclosure.

What is claimed is:

1. A method for preparing a natural organic macromolecular water treatment agent, comprising:
    S1, dissolving amylose corn starch in an alkali solution, stirring for 30 min, to obtain a suspension, and freezing the suspension to a fully frozen state, to obtain a frozen product, melting the frozen product, and subjecting the melted frozen product to a dialysis treatment, to obtain a corn starch dispersion;
    S2, mixing 50 mg of a modified flax fiber, 50 mg of the corn starch dispersion, 20 mg of a nano-hybrid silica and 5 mL of distilled water, to obtain a mixture, and subjecting the mixture to an ultrasonic treatment with 800 W for 10 min, to obtain an ultrasonic treated suspension;
    S3, taking an appropriate amount of a superabsorbent macromolecular resin with a certain shape, making the superabsorbent macromolecular resin fully absorb water and swell, to form a solid hydrogel with the certain shape;
    S4, uniformly mixing the solid hydrogel and the ultrasonic treated suspension in a mass ratio of 1:(2.5-10.5), subjecting the resulting mixture to a static defoaming, loading into a mold and solidifing, and drying until the solid hydrogel was completely dehydrated, to obtain a hollow water treatment agent; and
    S5, spraying a catalytic degrading agent and/or toxin degrading agent on the surface of the hollow water treatment agent and/or the inner wall of holes thereof, to obtain the natural organic macromolecular water treatment agent.

2. The method for preparing a natural organic macromolecular water treatment agent of claim 1, wherein in the step S1, the freezing is performed at a temperature of −5° C. to −15° C., and the freezing is performed for 30-50 min, and the melting is performed at ambient temperature and pressure.

3. The method for preparing a natural organic macromolecular water treatment agent of claim 1, wherein the modified flax fiber is prepared by the steps of:
    washing a waste flax residue, and placing in an oven at 70° C. and drying to a constant weight, crushing, and sieving with a 200 mesh sieve, to obtain a flax powder; and
    immersing 3-5 parts by mass of the flax powder into 20-30 parts by mass of a NaOH solution with a mass concentration of 1 mol/L, to obtain a mixture, placing the mixture on a heating magnetic stirrer for magnetic stirring for 10 hours, and filtering, to obtain a filter residue, rinsing the filter residue with deionized water until the pH of rinse water is close to neutral, drying in a oven at 80° C., naturally cooling to ambient temperature, and drying in a drying oven, to obtain the modified flax fiber.

4. The method for preparing a natural organic macromolecular water treatment agent of claim 1, wherein the nano-hybrid silica is a nano-$SiO_2$ hybrid particle grafted with a chain segment of polyhydroxyethyl acrylate (PHEA) and polystyrene (PS).

5. The method for preparing a natural organic macromolecular water treatment agent of claim 1, wherein in the step S3, the superabsorbent macromolecular resin is selected from the group consisting of polyacrylic acid salt, polyvinyl alcohol, polyoxylated alkanes and cellulose.

6. The method for preparing a natural organic macromolecular water treatment agent of claim 1, wherein the toxin degrading agent is toxin degrading enzyme and/or toxin degrading bacteria.

* * * * *